United States Patent
Trapp et al.

(10) Patent No.: US 6,653,148 B2
(45) Date of Patent: Nov. 25, 2003

(54) OPTICAL SENSOR FOR DETERMINING AN ANALYTE, AND METHOD OF MANUFACTURING THE OPTICAL SENSOR

(75) Inventors: Thilo Trapp, Affoltern am Albis (CH); Klaus-Dieter Anders, Würenlos (CH); Christian Huber, Abensberg (DE); Ingo Klimant, Mintraching (DE)

(73) Assignee: Mettler-Toledo GmbH, Greifensee (CH)

( * ) Notice: Subject to any disclaimer, the term of this patent is extended or adjusted under 35 U.S.C. 154(b) by 43 days.

(21) Appl. No.: 09/981,659

(22) Filed: Oct. 16, 2001

(65) Prior Publication Data

US 2003/0017078 A1 Jan. 23, 2003

(30) Foreign Application Priority Data

Oct. 16, 2000 (DE) ......................... 100 51 220

(51) Int. Cl.⁷ .............................. G01N 21/64
(52) U.S. Cl. ............... 436/172; 422/82.07; 422/82.08
(58) Field of Search .................. 422/82.07, 82.08, 422/82.11; 250/458.1, 459.1; 436/172, 136, 138

(56) References Cited

U.S. PATENT DOCUMENTS

| | | | | | |
|---|---|---|---|---|---|
| 4,206,132 A | * | 6/1980 | Sievers | ................ | 534/15 |
| 4,842,783 A | * | 6/1989 | Blaylock | .............. | 264/1.27 |
| 5,152,287 A | * | 10/1992 | Kane | ................... | 600/364 |
| 6,139,798 A | * | 10/2000 | Klimant et al. | ......... | 422/82.07 |
| 6,329,205 B1 | * | 12/2001 | Diwu et al. | ............. | 436/86 |
| 6,432,363 B2 | * | 8/2002 | Biebernik et al. | ....... | 422/82.07 |

FOREIGN PATENT DOCUMENTS

WO    WO 93/18391    *   9/1993

* cited by examiner

Primary Examiner—Jeffrey Snay
(74) Attorney, Agent, or Firm—Friedrich Kueffner

(57) ABSTRACT

An optical sensor for determining an analyte, specifically oxygen, has a sensor matrix that is made up substantially of a fluoropolymer. The sensor matrix contains a luminescent indicator with a metal complex of ruthenium, rhenium, rhodium or iridium, and with at least one at least partially fluorinated ligand.

19 Claims, 6 Drawing Sheets

(A)

(B)

(C)

(D)

(E)

(F)

(G)

(H)

(J)

(K)

(L)

Figures 5 (M) and 5(N)
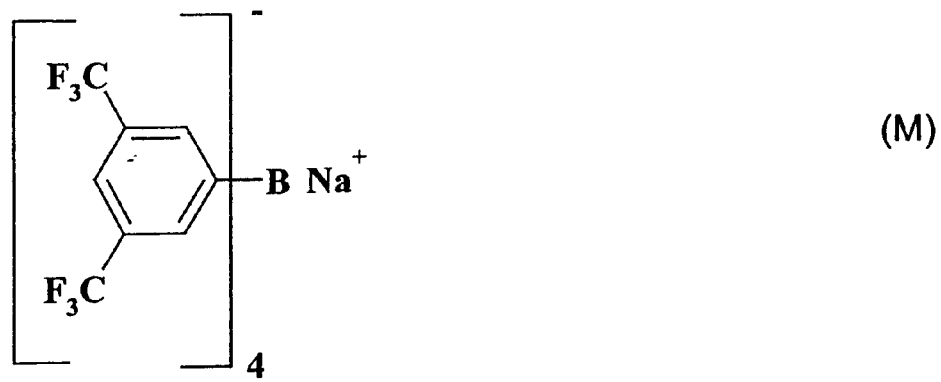
(M)
(N)

OPTICAL SENSOR FOR DETERMINING AN ANALYTE, AND METHOD OF MANUFACTURING THE OPTICAL SENSOR

BACKGROUND OF THE INVENTION

1. Field of the Invention

The invention relates to an optical sensor for determining an analyte, specifically oxygen, with a sensor matrix that is formed substantially of a fluoropolymer and contains a luminescent indicator. In addition, the invention also relates to a method of manufacturing the sensor, a method of determining an analyte in a measuring medium, as well as an application of the optical sensor.

2. Prior Art Related to the Invention

Optical sensors are used in the most diverse fields of application to detect the presence of certain analytes in a measuring medium and in particular to measure their concentration. Examples of such analytes are oxygen, carbon dioxide, sulfur dioxide, as well as other chemical substances that are contained in a liquid or gaseous measuring medium, e.g., in an aqueous solution, in air, and other media.

Optical sensors within the same general field as the present invention are described in WO-93/18391 and U.S. Pat. No. 5,152,287, and also in a dissertation, "Optical Sensors for Trace Oxygen Analysis", by Martina Trinkel, Department of Natural Science, Karl Franzens University, Graz, July 1998 (which will subsequently be referred to as the "Trinkel dissertation"). The optical sensors described in these references have a sensor matrix that is formed essentially of a fluoropolymer and contains a luminescent indicator. The luminescent indicator has the ability to be excited by light and to return some of the absorbed light energy as luminescent radiation, wherein one or more measurable properties, including the intensity or the decay period of the luminescence, are variable in response to the analyte that is to be determined. Because of the permeability of the sensor matrix for the analyte, a high analyte concentration in the measuring medium will cause a correspondingly high analyte concentration in the sensor matrix and thus manifest itself by a strong change in the luminescent properties, which can for example be expressed through the known Stern-Volmer equation. In principle, a measurement of the luminescent properties can be used to draw conclusions regarding the concentration of the analyte in the measuring medium.

The main requirements for a sensor matrix include a high degree of transparency for the light used to excite the luminescent indicator as well as for the radiation emitted by the luminescent indicator, a sufficient degree of permeability for the analyte, as well as mechanical and chemical durability.

The optical sensors described in WO-93/18391, which are intended in particular for the detection of oxygen or carbon dioxide in a fluid measuring medium, have a sensor matrix that is formed of a hardened, partially fluorinated polyurethane and contains a luminescent indicator of a known kind. In U.S. Pat. No. 5,152,287, a sensor matrix is described that is formed of a partially fluorinated polyacrylate and likewise contains a luminescent indicator of a known kind. In the manufacturing process of these known sensor matrices, the luminescent indicator used in each case, preferably a transition metal complex, is mixed with the basic materials required for producing the fluoropolymer, normally a precursor substance and a hardener substance. Subsequently, the fluoropolymer with the locked-in luminescent indicator is formed by thermal or light-induced cross-linking.

The known sensors described above suffer from the drawback that the fluoropolymer used in them as a matrix material does not have the chemical and/or mechanical durability required for certain applications. However, the use of a chemically and/or mechanically more durable fluoropolymer such as poly-tetrafluoro-ethylene or one of its known derivatives is made difficult, if not impossible, by the fact that the known luminescent indicators cannot be incorporated at all in the more durable fluoropolymer, or only with considerable difficulty. In particular, the known luminescent indicators are difficult to dissolve or totally insoluble in highly fluorinated or even perfluorinated polymers, so that a homogeneous distribution of the luminescent indicator molecules in the sensor matrix is difficult or even impossible to achieve. As a particular disadvantage, an aggregation of luminescent indicator molecules which takes place in a time span of days to weeks will cause a noticeable change of the optical sensor properties. In addition, one often observes a highly undesirable escape of the luminescent indicator from the sensor matrix. Prototypes of optical sensors for analyzing gases that are present in trace amounts are described in the Trinkel dissertation, where the sensor matrix consists of a copolymer formed of tetrafluoro-ethylene and 2,2-bis-trifluoromethyl-4,5-difluoro-1,3-dioxol. Fluoropolymers of this kind are known and available, e.g., under the trade name of Teflon® AF, in particular Teflon® AF 1600 or Teflon® AF 2400. A variety of known complexes of tin, palladium, and platinum-porphyrin, among others, were used as luminescent indicators in Trinkel's work. As described in detail in the Trinkel dissertation, (see in particular chapter 4.4.6., "Storage Stability") the sensor prototypes under investigation showed an undesirable escape of the luminescent indicator from the sensor matrix. Consequently, the investigated optical sensors, because of their inadequate durability, had to be rejected as being not suitable for process-monitoring (see last sentence of chapter 4.5., "Conclusion").

The methods that have until now been used in manufacturing the types of sensors described above are based on introducing the luminescent indicator already before forming the fluoropolymer. This has the disadvantage that during the polymerization process, the aforementioned non-homogeneous distribution of the luminescent indicator can occur while, on the other hand, the luminescent indicator may even be destroyed by the highly reactive radicals that participate in the polymerization. Furthermore, the known processes are expensive, they involve handling of toxic substances, and their reproducibility is poor. The Trinkel dissertation describes how attempts were made to circumvent these problems by using Teflon® AF, which is soluble in highly fluorinated and perfluorinated solvents, as a matrix material. As mentioned above, the attempt was unsuccessful because the resulting sensor matrices did not have the desired properties and in particular, because they showed an aggregation of the luminescent indicator and/or an escape of the luminescent indicator material from the sensor matrix.

OBJECT OF THE INVENTION

The object of the present invention is to provide an improved optical sensor, as well as a method of manufacturing the sensor, that are free of the aforementioned drawbacks.

Further objects of the invention are to provide a method of determining an analyte in a measuring medium and to describe a use of the optical sensor according to the invention.

SUMMARY OF THE INVENTION

An improved optical sensor for determining an analyte, particularly for determining oxygen, with a sensor matrix that is formed substantially of a fluoropolymer and contains a luminescent indicator, is distinguished by the fact that the luminescent indicator contains a metal complex of ruthenium, rhenium, rhodium or iridium, and at least one at least partially fluorinated ligand.

In a method of manufacturing the optical sensor according to the invention, a quantity of the luminescent indicator and a quantity of the fluoropolymer are dissolved in a solvent, and the sensor matrix is formed subsequently by evaporating the solvent.

Further according to the invention, a method of determining an analyte in a measuring medium is based on the concept of bringing the inventive sensor into contact with the measuring medium and by detecting or measuring a change of an optical property of the luminescent indicator that is caused by an interaction with the analyte.

Lastly, the scope of the invention also covers the use of the inventive sensor for detecting or measuring oxygen in a liquid or gaseous medium.

With a luminescent indicator which, in accordance with the invention, contains a metal complex of ruthenium, rhenium, rhodium or iridium and at least one partially fluorinated ligand, the luminescent indicator can be introduced significantly better into fluoropolymers of all kinds. Thus, the selection of a particular fluoropolymer can be adapted to the range of applications for which the optical sensor is intended. In particular, the invention makes it possible to use highly fluorinated or even perfluorinated polymers. The metal complexes proposed by the invention with at least partially fluorinated ligands are distinguished by good solubility in fluoropolymers. Thus, they ensure a thermodynamically stable, homogeneous distribution of the luminescent indicator in the sensor matrix. As a result, the optical sensor according to the invention has a high degree of constancy and durability.

In the inventive method of manufacturing the sensor, a quantity of the luminescent indicator and a (different) quantity of the fluoropolymer are dissolved in a solvent, and the sensor matrix is subsequently formed by evaporating the solvent. In contrast to the known methods, the manufacturing process according to the invention uses a fluoropolymer procured in pre-manufactured form from a supplier. Because no polymerization processes have to be performed in the manufacture of the sensor, the inventive manufacturing method is simple to carry out, has good reproducibility, and in addition does not require the handling of toxic substances. In addition, the method according to the invention avoids the problem of the luminescent indicator being broken down by the radicals that participate in the polymerization processes and by other highly reactive species.

According to a preferred embodiment of the invention, the sensor matrix is formed of fluoropolymer which, in essence, is room-temperature soluble only in highly fluorinated or perfluorinated solvents. Preferably, the sensor matrix is formed of a derivative of poly-tetrafluoro-ethylene. Because the fluoropolymer is soluble exclusively in those solvents, there is assurance that the sensor matrix will not be dissolved or swell up on contact with another solvent that may be present in particular in the measuring medium. Particularly preferred is an embodiment of the invention where the fluoropolymer is a copolymer formed of tetrafluoro-ethylene and 2,2-bis-trifluoromethyl-4,5-difluoro-1,3-dioxol. Fluoropolymers of this kind are known, e.g., under the trade name of Teflon® AF, in particular Teflon® AF 1600 or Teflon® AF 2400, and are distinguished by a high degree of solubility in selected highly fluorinated or perfluorinated solvents. The high transparency of these fluoropolymers is a favorable factor for the optical excitation of the luminescent indicator and for the detection of the luminescent radiation. In addition, the high degree of permeability to gases assures a rapid response to changes in the concentration of the analyte in the measuring medium.

The scope of the invention also covers advantageous embodiments of the metal complex. Primarily two-pronged chelate ligands are proposed as ligands for the metal complex, with particular preference for the group of polypyridines, particularly the group of substituted 1,10-phenanthrolin derivatives and substituted bipyridines containing at least one at least partially fluorinated substituent. In particular, a 4,7-dipentafluoro-benzyloxy-1,10-phenanthrolin may be used as a ligand. An alternative choice for a ligand can consist of a 5-pentafluoro-benzamide-1,10-phenanthrolin; a 4,7-di-(3,3,4,4,5,5,5-heptafluoro-pentyl)-1,10-phenanthrolin; an N,N'-di-(2,2,3,3,4,4,4-heptafluorobutyl)-1,10-phenanthrolin-4,7-diamide; or a 4,7-di-2,2,3,3,4,4,4-heptafluoro-butyl-amino-1,10-phenanthrolin. Another possible alternative for a ligand is a 4,4'-di-(3,3,4,4,5,5,5-heptafluoropentyl)-2,2'-bipyridine or an N,N'-di-(2,2,3,3,4,4,4-heptafluorobutyl)-4,4'-bipyridine-2,2'-diamide. The metal complex can contain either a plurality of identical ligands or a plurality of different ligands. The preferred choice of a metal complex is a ruthenium(II)-tris-(4,7-dipentafluoro-benzyloxy-1,10-phenanthrolin; or a ruthenium(II)-bis-(4,7-diphenylphenanthrolin)-(4,7-dipentafluoro-benzyloxy-1,10-phenanthrolin); or a ruthenium(II)-bis-(4,7-dipentafluoro-benzyloxy-1,10-phenanthrolin)-(4,7-diphenyl-phenanthrolin).

In one embodiment of the invention, the luminescent indicator contains an at least partially fluorinated counter ion, which results in improved solubility of the luminescent indicator in the fluoropolymer that forms the sensor matrix. Particularly advantageous is an embodiment in which the counter ion is suitable for causing a steric hindrance. Examples of anions with this property are tetrakis-(4-chlorophenyl)-borate; tetrakis-[3,5-bis-(trifluormethyl)-phenyl]-borate; and tetrakis-[3,5-bis-(1,1,1,3,3,3-hexafluor-2-methoxy-2-propyl)-phenyl]-borate, which because of their bulk present a further obstacle to an undesirable aggregation of the luminescent indicator.

In a further advantageous embodiment, the sensor matrix is configured in the shape of a foil. This makes for a short entry path of the analyte into the sensor matrix, so that the optical sensor will have a rapid response.

In another embodiment, the sensor matrix is provided with a protective layer consisting substantially of the same fluoropolymer as the sensor matrix but containing essentially no luminescent indicator material. This serves to avoid a direct contact between peripheral portions of the sensor matrix and the measuring medium, so as to prevent mechanical damage to the sensor matrix from abrasive particles of the measuring medium and/or a reaction of the luminescent indicator with substances contained in the measuring medium.

A preferred version of the manufacturing method for the optical sensor involves the use of a highly fluorinated or perfluorinated solvent, e.g., octafluorotoluol, which has strong solvent capabilities for the fluoropolymers used in forming the sensor matrix as well as for the metal complexes with fluorinated ligands that are used as luminescent indicators.

BRIEF DESCRIPTION OF THE DRAWING

Embodiments of the invention are described below on the basis of the drawings, wherein.

DETAILED DESCRIPTION OF THE INVENTION

1. Fundamental Elements of the Invention

Figure 1:
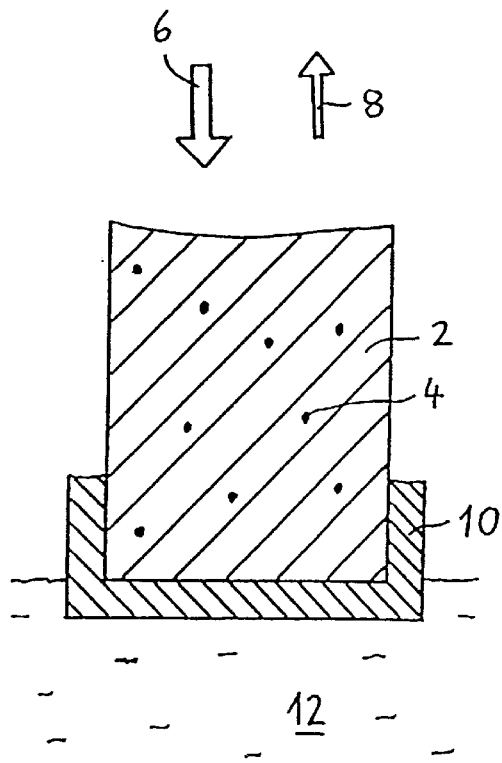
FIG. 1 represents a part of an optical sensor in a schematic view, in a lengthwise section.

FIG. 1 illustrates a part of an optical sensor with a sensor matrix 2 formed of a fluoropolymer and containing a luminescent indicator 4. The luminescent indicator 4 has the ability to be excited by incoming light radiation 6 and to return part of the absorbed light energy in the form of a luminescent radiation 8. As a practical consideration, the sensor matrix 2 is surrounded by a protective layer 10 that consists of substantially the same fluoropolymer as the sensor matrix 2, but is essentially free of the luminescent indicator material 4. The protective layer 10 serves to prevent a direct contact between the sensor matrix 2 and a (schematically indicated) measuring medium 12.

Figure 2:
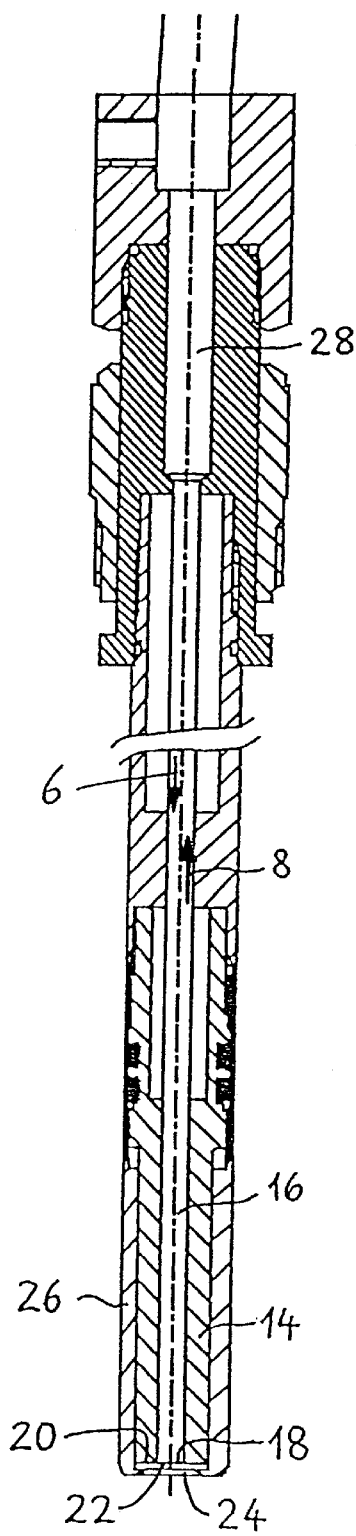
FIG. 2 represents an optical sensor in a lengthwise sectional view.

FIG. 2 illustrates an optical sensor with a tubular housing 14 containing a glass rod 16 with a polished end surface 18, where the latter together with the end surface 20 of the housing 14 forms a support surface for a sensor matrix 22 that is configured in the shape of a foil. On the side of the sensor matrix 22 that faces away from the support surface 18, 20, a cover foil 24 is arranged to work as a protective layer. The cover foil 24 and the sensor matrix 22 are clamped in place against the support surface by a retaining sleeve 26. The glass rod 16 works as a means of introducing the incoming light 6 as well as returning the luminescent radiation 8. At the opposite end of the glass rod 16, a light conductor 28 is provided, e.g., a bundle of optical fibers, whereby an optical connection to a light source (not shown) and a light detector (likewise not shown) can be established.

To detect or measure an analyte in a measuring medium, a change of an optical property of the luminescent indicator is determined in a known manner. The change is caused by an interaction between the luminescent indicator and a portion of the analyte that has penetrated the sensor matrix. It is known that the intensity as well as the decay period of the luminescence of certain luminescent indicators is reduced as a result of a dynamic extinguishing effect (quenching) caused by certain analytes, e.g. oxygen. This phenomenon is expressed in the Stern-Volmer equation:

$$F_o/F=\tau_o/\tau=1+k\tau_o\cdot[Q]=1+K_{SV}[Q] \quad (1)$$

In the foregoing equation, $F_o$ and $F$ stand for the respective relative intensities of the luminescence in the absence and presence of an analyte, $[Q]$ stands for the concentration of the analyte, $k$ stands for the bimolecular rate constant for quenching the luminescence, $\tau_o$ and $\tau$ stand for the respective decay times of the luminescent radiation in the absence and presence of the analyte, and $K_{SV}$ stands for the Stern-Volmer quenching constant. Thus, the ratio $F_o/F$ or $\tau_o/\tau$ can be used to draw a conclusion regarding the analyte concentration present in the sensor matrix which, in turn, is within a large measuring range proportionate to the analyte concentration in the measuring medium. It is known, however, that in certain cases the observed luminescent response will deviate from predictions that are based on the Stern-Volmer equation. In many cases, it is possible to use a modified model with a superposition of two or more Stern-Volmer equations with different quenching constants. As a matter of good practice, the optical sensor is therefore calibrated in a known manner, at least prior to its first use and preferably at regular intervals thereafter.

In a manufacturing method for the sensor matrix, the luminescent indicator, which is preferably a complex salt formed by a metal complex with a counter ion, is dissolved in an appropriate medium, preferably a highly fluorinated or perfluorinated solvent. Next, a fluoropolymer that is soluble in the same solvent is added to the solution, e.g., in a proportion of 5% of the weight of the solvent. After a homogeneous solution of luminescent indicator and fluoropolymer has been obtained in this manner, it is brought into the desired shape by pouring or by spreading with a spatula. The solvent is subsequently removed either by letting it evaporate on its own or by vaporizing it, whereby the sensor matrix is formed.

The fluoropolymer that is used with preference is a copolymer formed of tetrafluoro-ethylene and 2,2-bis-trifluoromethyl-4,5-difluoro-1,3-dioxol, which is known, e.g., under the trade name of Teflon® AF. This material is chemically inert; and it is distinguished by a high permeability for gas and a good level of optical transparency in the infrared to ultraviolet range of the spectrum. At room temperature, Teflon® AF is soluble only in certain highly fluorinated or perfluorinated solvents such as octa-fluorotoluol or perfluorodecalin. Teflon® AF is available in different compositions, including Teflon® AF 1600 with a dioxol content of 65 mole percent and Teflon® AF 2400 with a dioxol content of 85 mole percent. In the manufacture of sensor matrices, Teflon® AF 1600 is preferred because of its superior solubility in comparison to Teflon® AF 2400.

2. Preferred Luminescent Indicators

Figure 5:
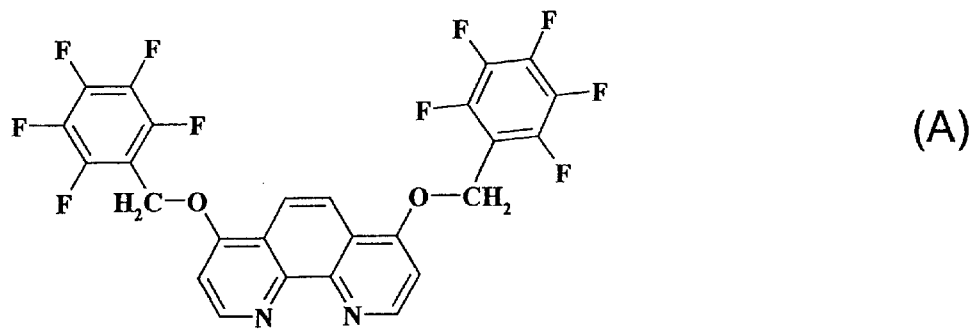
FIGS. 5(A) to 5(N) represent the molecular structures of ligands used in luminescent indicators.
Figure 5:
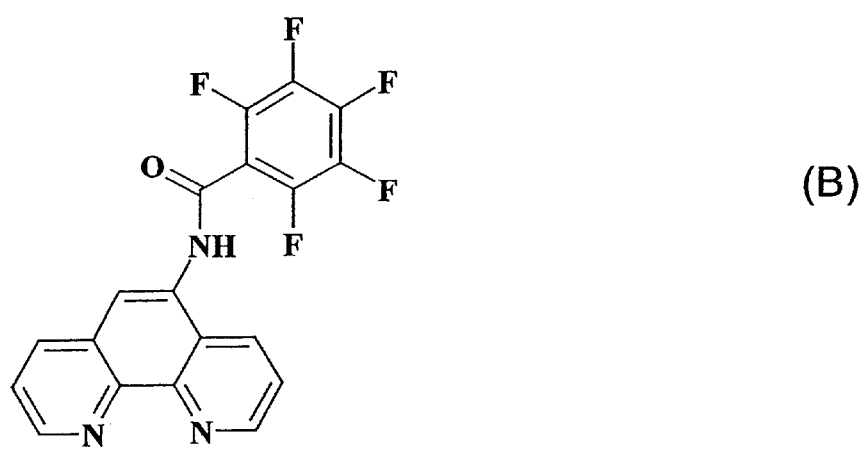
Figure 5:
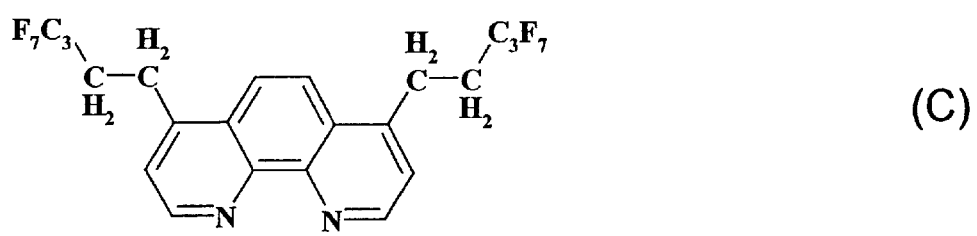
Figure 5:
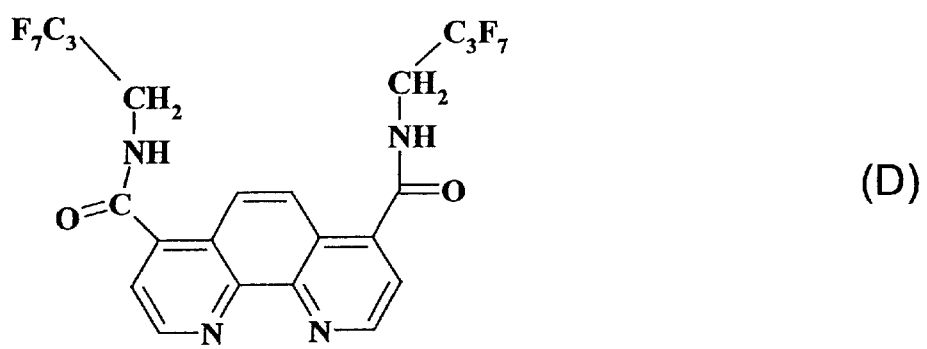
Figure 5:
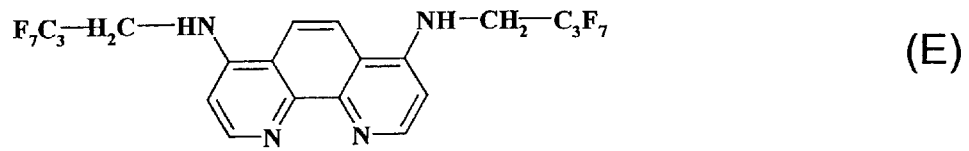
Figure 5:
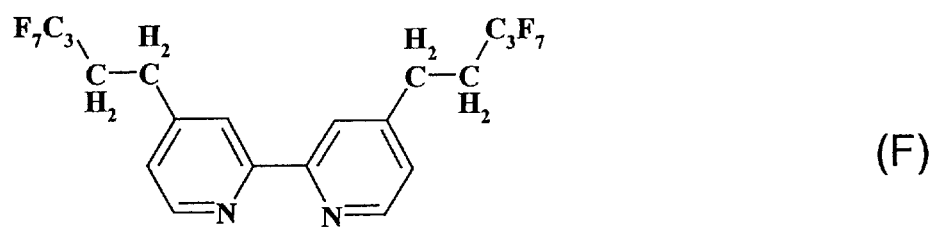
Figure 5:
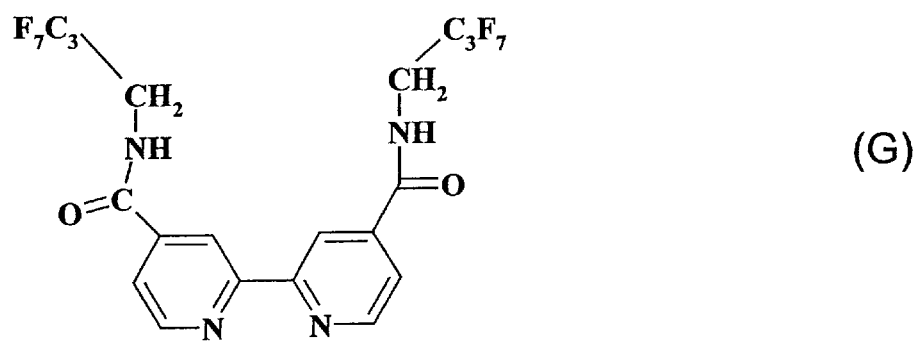
Figure 5:
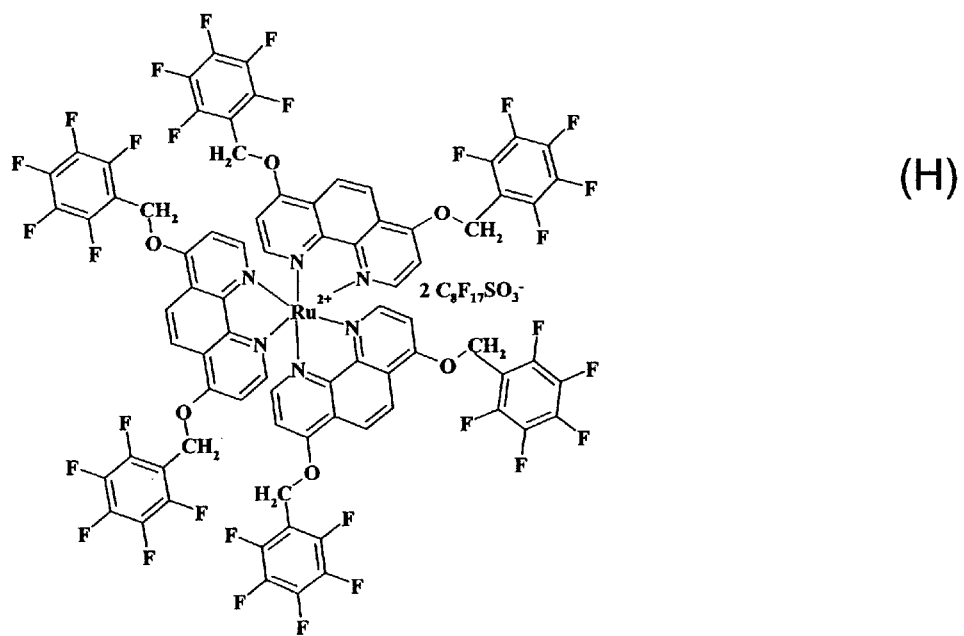
Figure 5:
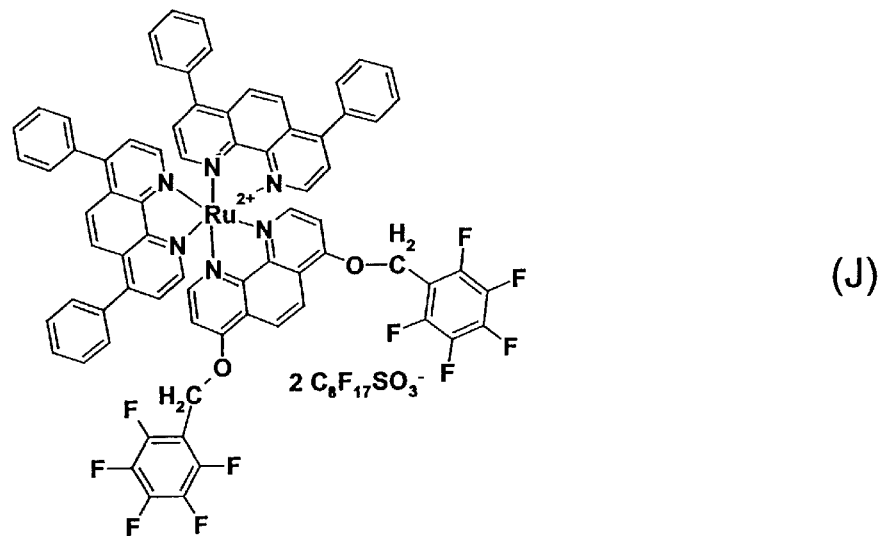
Figure 5:
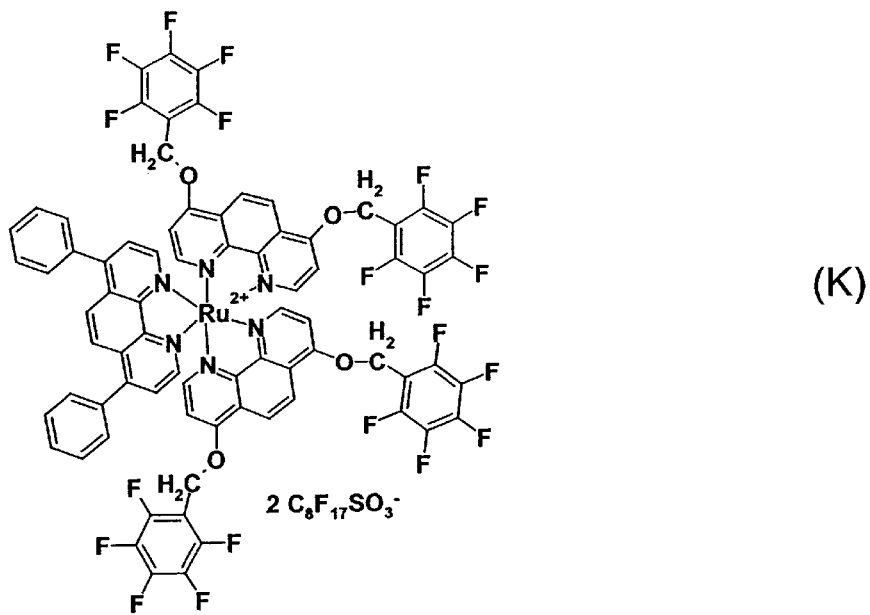
Figure 5:
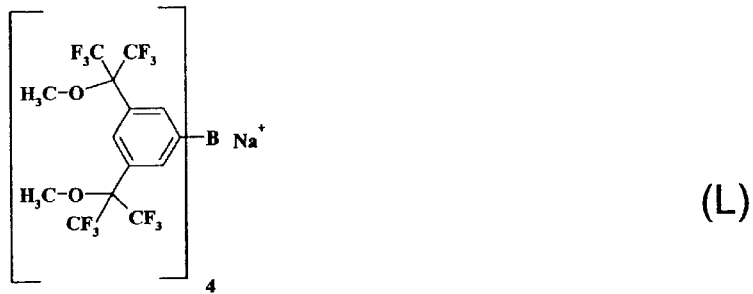

The following ligand (A), whose molecular structure is shown in FIG. 5(A), is particularly suitable in the manufacture of luminescent indicators:

Name: 4,7-dipentafluoro-benzyloxy-1,10-phenanthrolin
Formula: $C_{26}H_{10}F_{10}N_2O_2$ Molecular weight: 572.4 g/mol)

Following are further examples of fluorinated ligands (B) through (G), whose molecular structures are illustrated in FIGS. 5(B) through 5(G), respectively:

(B) Name: 5-pentafluorobenzamide-1,10-phenanthrolin;
Formula: $C_{19}H_8F_5N_3O$ Molecular weight: 389.3 g/mol
(C) Name: 4,7-di-(3,3,4,4,5,5,5-heptafluoropentyl)-1,10-phenanthrolin;
Formula: $C_{22}H_{14}F_{14}N_2$ Molecular weight: 572.34 g/mol
(D) Name: N,N'-di-(2,2,3,3,4,4,4-heptafluorobutyl)-1,10-phenanthrolin-4,7-diamide
(E) Name: 4,7-di-2,2,3,3,4,4,4-heptafluoro-butylamino-1,10-phenanthrolin:
(F) Name: 4,4'-di-(3,3,4,4,5,5,5-heptafluoropentyl)-2,2'-bipyridine
(G) Name: N,N'-di-(2,2,3,3,4,4,4-heptafluorobutyl)-4,4'-bipyridine-2,2-diamide The foregoing ligands can form metal complexes with ruthenium, rhenium, rhodium or iridium, which can be isolated and stored as complex salts together with a suitable counter ion.

The following examples (H) through (N) of preferred luminescent indicators are shown as complex salts in FIGS. 5(H) through 5(N).

(H) Name: Ruthenium(II)-tris-(4,7-dipentafluoro-benzyloxy-1,10-phenanthrolin)-diperfluoro-octylsulfonate
Formula: $RuC_{94}H_{30}F_{64}N_6O_{12}S_2$ Molecular wt.: 2816.37 g/mol The foregoing complex contains three identical ligands of 4,7-dipentafluoro-benzyloxy-1,10-phenanthrolin (abbreviated below as dpfbp). Instead of one, two or three dpfbp ligands, the complexes named below contain one or two conventional, non-fluorinated ligands of 4,7-diphenyl-phenanthrolin (abbreviated below as dpp).

(J) Name: Ruthenium(II)-bis-(4,7-diphenylphenanthrolin)-(4,7-dipentafluoro-benzyloxy-1,10-phenanthrolin)-diperfluoro-octylsulfonate
Abbr.: $Ru(dpp)_2(dpfbp) (PFOS)_2$
Formula: $RuC_{90}H_{42}F_{44}N_6O_8S_2$ Molecular wt.: 2336.52 g/mol (K) Name: Ruthenium(II)-bis-(4,7-dipentafluorobenzyloxy-1,10-phenanthrolin)-(4,7-diphenylphenanthrolin)-diperfluorooctylsulfonate
Abbr.: $Ru(dpp) (dpfbp)_2(PFOS)_2$
Formula: $RuC_{96}H_{26}F_{54}N_6O_{10}S_2$ Molecular wt.: 2576.4 g/mol A borate anion may be used as counter ion instead of the perfluoro-octylsulfonate anion (subsequently abbreviated as PFOS) that is contained in the foregoing luminescent indicators. Following are the sodium salts of particularly preferred counter ions:

(L) Name: Sodium-tetrakis-[3,5-bis-(1,1,1,3,3,3-hexafluor-2-methoxy-2-propyl)-phenyl]-borate trihydrate
Formula: $C_{56}H_{36}BF_{48}O_8Na.3H_2O$ Molecular wt.: 1836.67 g/mol (M) Name: Sodium-tetrakis-[3,5-bis-(trifluormethyl)-phenyl]-borate
Formula: $C_{32}H_{12}BF_{24}Na$ Molecular wt.: 886.2 g/mol The foregoing anions, particularly the anion of example (L), are distinguished by their considerable bulkiness, causing a steric hindrance that strongly restricts the diffusion of the luminescent dye substance in the sensor matrix and presents a significant obstacle to an undesirable aggregation or an escape of the luminescent dye from the sensor matrix. Furthermore, the at least partial fluorination of these counter ions increases the solubility of the corresponding luminescent indicators in highly fluorinated or perfluorinated fluoropolymers.

The following chlorinated borate anion, shown in a potassium salt, represents a more cost-effective alternative in comparison to (L) und (M).

(N) Name: Potassium-tetrakis-(4-chlorphenyl)-borate
Formula: $C_{24}H_{16}BCl_4K$ Molecular wt.: 496.12 g/mol Depending on the particular metal complex that is being used and the fluoropolymer that forms the sensor matrix, one will need to evaluate in preliminary tests whether the aforementioned anion (N), although it is not fluorinated, provides a degree of solubility and stability of the luminescent indicator in the sensor matrix that is adequate for the intended application, or whether one of the fluorinated anions (L) or (M) would be preferable.

3. Methods of Synthesis:

The luminescent indicators discussed herein are produced by conventional methods. As an example for the manufacture of a preferred luminescent indicator, the synthesis of $Ru(dpp)_2(dpfbp)(PFOS)_2$ is described in the following sections.

3.1. Synthesis of 4,7-dipentafluoro-benzyloxy-1,10-phenanthrolin (dpfbp)

A quantity of 0.2 g (0.94 mmol) of 4,7-dihydroxy-1,10-phenanthrolin was dissolved in 10 mL of N,N-Dimethylformamide in a 100 mL flask equipped with a counterflow cooler. Next, 0.12 g (3 mmol) of sodium hydride (60%, in oil) was added, after having been washed 4 times in petroleum ether to remove the oil. The resulting slurry was stirred for 30 minutes at 25° C., whereupon 624 mg (2.39 mmol) of pentafluoro-benzyl-bromide was added. The temperature was then raised to 60° C. and held constant for three hours. After cooling down, the mixture was put into 100 mL of water and an extraction was made with three times 80 mL of dichloro-methane. The combined organic phases were dried with sodium sulfate, concentrated under vacuum and recrystallized in a 1:1 mixture of dichloro-methane diethyl ether. The yield was 85 mg (0.15 mmol, 15.8%) of 4,7-dipentafluoro-benzyloxy-1,10-phenanthrolin in the form of a slightly colored solid. The characterization by $^1H$—NMR (nuclear magnetic resonance) in $CD_2Cl_2$ produced the following signals: δ=8.99 (d, J=5.3 Hz, 2H, aromatic), 8.07 (s, 2H, aromatic), 7.17 (d, J=5.3 Hz, 2H, aromatic), 5.43 (s, 4H, Ph—$CH_2$—O).

3.2. Synthesis of $Ru(dpp)_2Cl_2$ $RuCl_3.H_2O$ (62.4 mg, 0.3 mmol) was dissolved in a mixture of 2 mL of ethylene glycol and 0.2 mL of water at 120° C. Next, 200 mg (0.6 mmol) of 4,7-diphenyl-1,10-phenanthrolin was added. The resulting mixture was heated to 160° C. in a container equipped with a counterflow cooler and held at this temperature for 45 minutes. After cooling down, the solution was dissolved in 5 mL of ethanol, filtered, and diluted with ethanol. The filtrate obtained from this procedure contains $Ru(dpp)_2Cl_2$ and $Ru(dpp)_3Cl_2$ as a raw mixture. The latter was split up by column chromatography, using neutral aluminum oxide as stationary phase. The desired intermediate product $Ru(dpp)_2Cl_2$ was obtained by using acetone as mobile phase, while $Ru(dpp)_3Cl_2$ was eluted by means of ethanol.

3.3. Synthesis of $Ru(dpp)_2(dpfbp) (PFOS)_2$ 20 mg (0.024 mmol) of $Ru(dpp)_2Cl_2$ and 16.4 mg (0.029 mmol) of 4, 7-dipentafluorobenzyloxy-1,10-phenanthrolin (dpfbp) were dissolved in a mixture of 1 ml ethylene glycol and 0.1 ml of water and heated for 2 hours with return flow. After cooling, the solution was dissolved in 2 ml of ethanol and then filtered. The resulting filtrate contains raw $Ru(dpp)_2(dpfbp) Cl_2$.

To replace the chloride ion by the desired perfluorinated counter ion, the raw $Ru(dpp)_2(dpfbp)Cl_2$ was dripped slowly into a quantity of 10 ml of a 1 mM aqueous solution of perfluoro-octyl-sulfonic acid. The result was a finely distributed, orange-colored precipitate. The latter was filtered and washed four times in distilled water, whereby the luminescent dye material was obtained as a red crystalline powder with a yield of 45% (25 mg, 0.01 mmol). The purity was confirmed by mass spectroscopy and thin-film chromatography.

4. Practical Examples

The luminescent indicator $Ru(dpp)_2(dpfbp)(PFOS)_2$ or $Ru(dpp)(dpfbp)_2(PFOS)_2$ was dissolved in octafluorotoluol, and by subsequently adding Teflon® AF 1600, a solution with a volume proportion of approximately 5% Teflon was prepared. The proportions of the indicator in relation to the Teflon® F 1600 are shown below in Table 1. The resultant mixtures were spread on a polyester foil, using a metal blade to form layers with a thickness of 250 μm or 125 μm, whereby foil-shaped sensor matrices of, repectively, 12 μm and 6 μm thickness were obtained after the solvent had been vaporized. The sensor matrices showed a slight orange coloration.

TABLE 1

Composition of the sensor matrices M1 and M2

| Matrix | Luminescent indicator | Milligrams if indicator per gram of Teflon |
|---|---|---|
| M1 | (J) Ru(dpp)$_2$(dpfbp) (PFOS)$_2$ | 2 |
| M2 | (K) Ru(dpp) (dpfbp)$_2$(PFOS)$_2$ | 2 |

For the characterization of the sensor matrices, the latter were placed into a thermostatted flow-through cell where they were exposed to sinusoidally modulated light of a wavelength of 470 nm and a modulation frequency of 45 kHz. The luminescent radiation emitted by the sensor matrix was detected by a known phase-sensitive method. The average decay time τ of the luminescent radiation was calculated according to the equation $$\tau = \frac{\tan \Phi}{2\pi \cdot f} \quad (2)$$

wherein f stands for the modulation frequency of the excitation light and Φ stands for the phase angle between the exciter radiation and the luminescent radiation. The decay time τ as determined by this measurement represents an average across all of the luminescent species.

Figure 3:
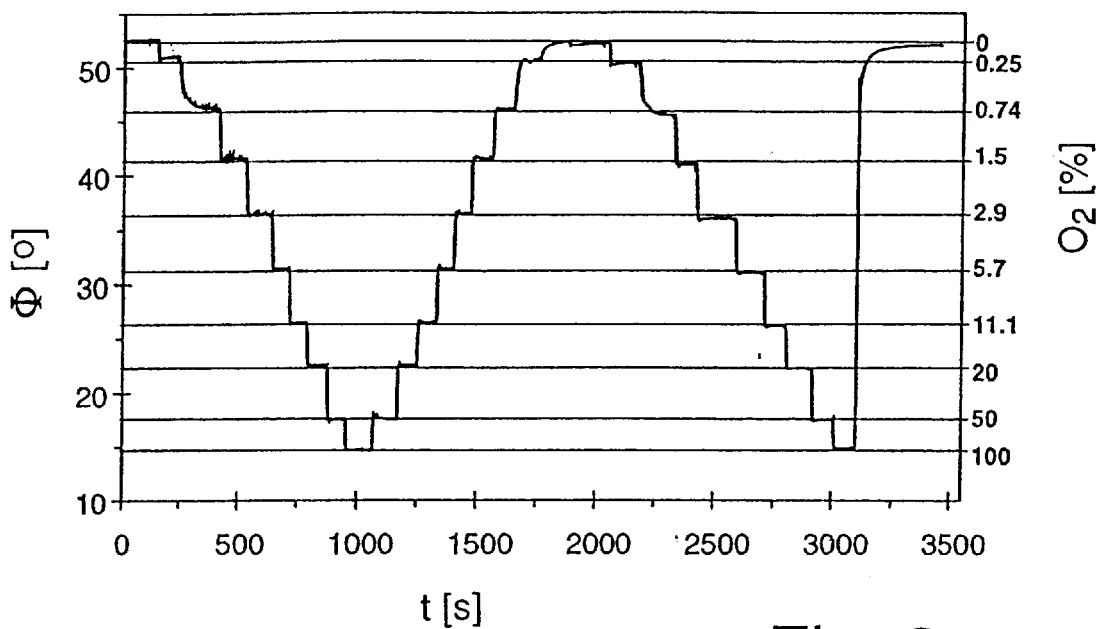
FIG. 3 represents the time profile of the optical phase shift of a sensor matrix with a repeated stepwise change of the oxygen content in a gaseous measuring medium.
Figure 4:
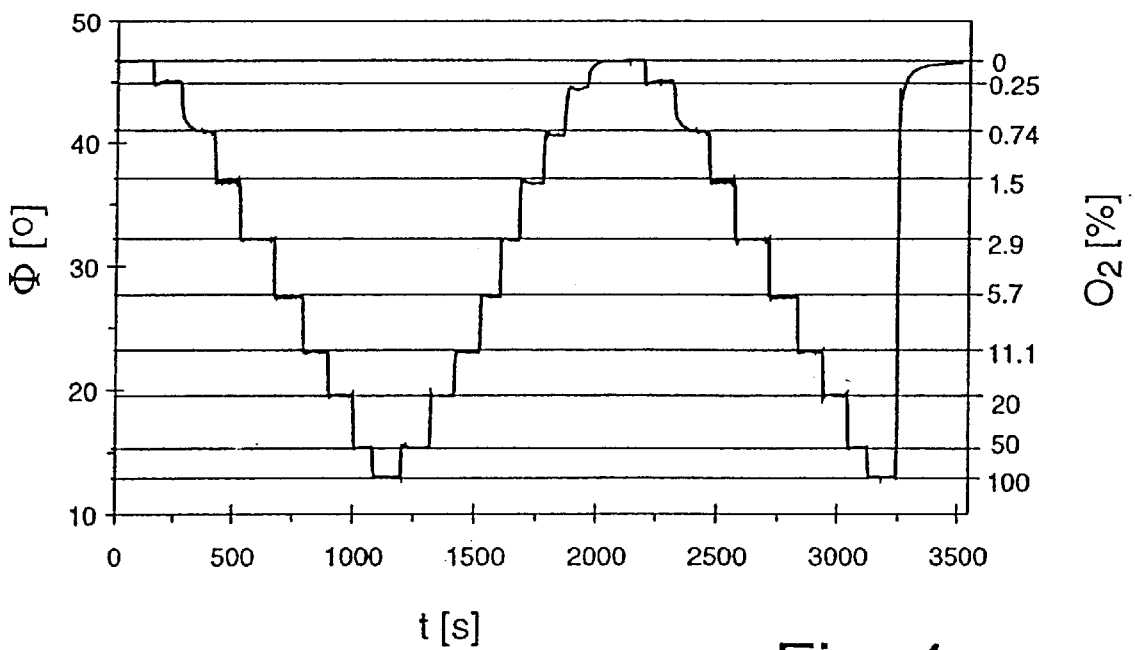
FIG. 4 represents the time profile of the optical phase shift of another sensor matrix with a repeated stepwise change of the oxygen content in the gaseous measuring medium.

For the characterization of the sensor matrices in a gaseous measuring medium, the prepared foils were exposed to a gas atmosphere of defined oxygen content, using dry as well as water-vapor containing ogygen/nitrogen mixtures. All measurements were made at a temperature of 22° C. FIGS. 3 and 4 show the response behavior of the phase angle Φ as a function of time with repeated stepwise decreases and increases of the oxygen content in a dry gaseous measuring medium. The results of the measurements demonstrate a rapid response time as well as good reproducibility.

The Stern-Volmer curves were determined in a known manner by plotting the relative luminescence intensity $F_o/F$ or the ratio $\tau_o/T$ as a function of the partial pressure $P(O_2)$ of oxygen, where the latter corresponds to the concentration of the analyte [Q] according to equation (1). As with other known optical sensors, the measured Stern-Volmer curves showed a certain amount of discrepancy from an ideal behavior. The results were therefore evaluated further by comparing the following three models:

(a) The linear model according to the equation $$\frac{\tau_0}{\tau} = 1 + K \cdot p(O_2) \quad (3)$$

represents the ideal behavior according to Stern-Volmer.
(b) The Carraway model according to the equation $$\frac{\tau_0}{\tau} = \left( \frac{f_1}{1 + K_1 \cdot p(O_2)} + \frac{f_2}{1 + K_2 \cdot p(O_2)} \right)^{-1} \quad (4)$$

is based on the assumption that the luminescent indicator occupies two different positions in the sensor matrix with different quenching constants $K_1$ and $K_2$, wherein the relative occupancy rates of the two positions are defined by the weight factors $f_1$ and $f_2$.

(c) In a simplified Carraway model according to the equation $$\frac{\tau_0}{\tau} = \left( \frac{f_1}{1 + K_1 \cdot p(O_2)} + f_2 \right)^{-1} \quad (5)$$

the luminescence of the indicator in the second position is assumed not to be quenchable ($K_2=0$).

In addition to evaluating the measurement data according to the equations (3) to (5), a further evaluation was made based on the relative intensity $F_o/F$ of the luminescence instead of the relative decay time $\tau_o/\tau$. The results of the evaluation are shown in Table 2.

TABLE 2

Quenching constants and weight factors of the sensor matrices M1 and M2

| Sensor matrix | Measured quantity | $K_1$ | $K_2$ | $f_1$ | $f_2$ | $R^2$ |
|---|---|---|---|---|---|---|
| M1, using eq. (3) | decay time | 0.0075 | — | 1 | — | 0.7345 |
| | intensity | 0.0118 | — | 1 | — | 0.8723 |
| M1, using eq. (4) | decay time | 0.0528 | 0.0008 | 0.701 | 0.299 | 0.9997 |
| | intensity | 0.0494 | 0.0012 | 0.790 | 0.210 | 0.9998 |
| M1, using eq. (5) | decay time | 0.0339 | — | 0.799 | 0.201 | 0.9933 |
| | intensity | 0.0324 | — | 0.889 | 0.111 | 0.9961 |
| M2, using eq. (3) | decay time | 0.0068 | — | 1 | — | 0.7306 |
| | intensity | 0.0085 | — | 1 | — | 0.7895 |
| M2, using eq. (4) | decay time | 0.0467 | 0.0007 | 0.695 | 0.305 | 0.9997 |
| | intensity | 0.0502 | 0.0009 | 0.728 | 0.272 | 0.9997 |
| M2, using eq. (5) | decay time | 0.0318 | — | 0.783 | 0.217 | 0.9949 |
| | intensity | 0.0320 | — | 0.830 | 0.170 | 0.9943 |

Best-fit calculations lead to the conclusion that the linear Stern-Volmer model of equation (3) does not give an adequate description of the results, as the correlation coefficient is significantly different from 1, i.e., $R^2<0.90$. The best representation was achieved by the Carraway model of equation (4), where $R^2>0.999$, but the simplified Carraway model of equation (5) also provided a good agreement of the experimental data ($R^2>0.99$). Consequently, the behavior of the sensor membranes under different external conditions can be conveniently assessed on the basis of the coefficients calculated according to equations (4) or (5).

4.1 The Effect of Humidity on the Measurement

When the results were compared between measurements made on a dry nitrogen/oxygen mixture and measurements made on a nitrogen/oxygen mixture saturated with water vapor at 22° C., there was only a slight discrepancy of 6% to 8% in the respective quenching constants $K_1$ and $K_2$. This advantageous behavior is attributed to the hydrophobic properties of the matrix material, which largely prevent the penetration of water into the sensor matrix. Consequently, a calibration of the optical sensor in the gas phase will also be suitable if the sensor is subsequently used in aqueous measuring media.

4.2 Tolerance of the Sensor Matrices M1 and M2 to Being Sterilized

It is indispensible for applications in connection with biological cell cultures or in medical research that the optical sensors can be sterilized, in order to avoid contamination of the measuring samples. In the present case, the sensor matrices M1 and M2 were evaluated with regard to the following cleaning and sterilization methods:

a) Autoclaving: Treatment with oversaturated steam of 130° C. at 1.5 times atmospheric pressure for one hour.
b) Alkali treatment (so-called "cleaning-in-place" (CIP)): Contact with an aqueous NaOH-solution (5%) at 90° C. for 15 minutes.

It was found that the sensor matrices M1 and M2 remained functional even after 10 cycles of one of the foregoing sterilization procedures and in particular did not suffer any loss of sensitivity. In addition, there was no formation of crystals of the luminescent indicator. It was noted, however, that the sensor matrix can separate itself from its polyester substrate under some circumstances. This problem can be avoided by roughening the contact surface of the polyester substrate prior to applying the matrix material. Furthermore, significant differences were found in the calibration curves after performing the sterilization. Consequently, it appears to be necessary to recalibrate the sensors after sterilizing.

Overall, the sensor matrices in the evaluation stand out in regard to their high sensitivity, a rapid response time, a good level of resistance to solvents, significant mechanical stability, as well as an excellent degree of tolerance to being sterilized.

LIST OF REFERENCE NUMBERS 2 sensor matrix
4 luminescent indicator
6 incoming light radiation
8 luminescent radiation
10 protective layer
12 measuring medium
14 housing
16 glass rod
18 end surface of 16
20 end surface of 14
22 sensor matrix
24 cover foil
26 retaining sleeve
28 light conductor

What is claimed is:

1. An optical sensor for determining an analyte, comprising a sensor matrix that is made up substantially of a first fluoropolymer containing a luminescent indicator, wherein the luminescent indicator comprises a metal complex of a metal selected from the group consisting of ruthenium, rhenium, rhodium and iridium, with at least one at least partially fluorinated ligand.

2. The optical sensor of claim 1, wherein the analyte comprises oxygen.

3. The optical sensor of claim 1, wherein at room temperature, the first fluoropolymer is soluble substantially exclusively in a solvent that is selected from the group consisting of highly fluorinated and perfluorinated solvents.

4. The optical sensor of claim 3, wherein the first fluoropolymer comprises a poly-tetrafluoro-ethylene derivative.

5. The optical sensor of claim 1, wherein the first fluoropolymer comprises a copolymer formed of tetra-fluoro-ethylene and 2,2-bis-trifluoro-methyl-4,5-difluoro-1,3-dioxol.

6. The optical sensor of claim 1, wherein the ligand comprises a substituted polypyridine with at least one at least partially fluorinated substituent.

7. The optical sensor of claim 1, wherein the ligand comprises one of a substituted 1,10-phenanthrolin derivative and a substituted bipyridine.

8. The optical sensor of claim 1, wherein the ligand comprises a 4,7-dipentafluoro-benzyl-oxy-1,10-phenantholin.

9. The optical sensor of claim 1, wherein the ligand is selected from the group that consists of 5-pentafluoro-benzamide-1,10-phenanthrolin; 4,7-di-(3,3,4,4,5,5,5-heptafluoropentyl)-1,10-phenanthrolin; N,N'-di-(2,2,3,3,4,4,4-heptafluorobutyl)-1,10-phenanthrolin-4,7-diamide; 4,7-di-2,2,3,3,4,4,4-heptafluorobutyl-amino-1,10-phenanthrolin; 4,4'-di-(3,3,4,4,5,5,5-heptafluoropentyl)-2,2'-bipyridine; and N,N'-di-(2,2,3,3,4,4,4-heptafluorobutyl)-4,4'-bipyridine-2,2'-diamide.

10. The optical sensor of claim 1, wherein the metal complex comprises a ruthenium(II)-tris-(4,7-dipentafluorobenzyloxy-1,10-phenanthrolin).

11. The optical sensor of claim 1, wherein the metal complex comprises a ruthenium(II)-bis-(4,7-dipentafluorobenzyloxy-1,10-phenanthrolin)-(4,7-diphenyl-phenanthrolin).

12. The optical sensor of claim 1, wherein the metal complex comprises a ruthenium(II)-bis-(4,7-diphenyl-phenanthrolin)-(4,7-dipentafluoro-benzyloxy-1,10-phenanthrolin).

13. The optical sensor of claim 1, wherein the luminescent indicator comprises an at least partially fluorinated counter ion.

14. The optical sensor of claim 13, wherein the counter ion is suitable for causing a steric hindrance.

15. The optical sensor of claim 1, wherein the sensor matrix is configured in the shape of a foil.

16. The optical sensor of claim 1, wherein the sensor matrix is provided with a protective layer of a second fluoropolymer that is substantially the same as the first fluoropolymer, and wherein the protective layer contains substantially none of the luminescent indicator.

17. A method of manufacturing the optical sensor of claim 1, comprising the steps of:
    a) dissolving a first quantity of the luminescent indicator and a second quantity of the first fluoropolymer in a solvent; and
    b) forming the sensor matrix by evaporating the solvent.

18. The method of claim 17, wherein the solvent is selected from the group consisting of highly fluorinated and perfluorinated solvents.

19. A method of determining an analyte in a measuring medium by means of the optical sensor of claim 1, comprising the steps of:
    a) bringing the optical sensor into contact with the measuring medium; and
    b) determining a change in an optical property of the luminescent indicator, said change being the result of an interaction between the analyte and the luminescent indicator.

* * * * *